United States Patent [19]

Abbott et al.

[11] Patent Number: 5,158,873
[45] Date of Patent: Oct. 27, 1992

[54] METHOD AND REAGENT FOR DETERMINING LD-1 ISOENZYME

[75] Inventors: William A. Abbott, Gurnee; David A. Yost, Round Lake Park; Rita S. Byrne, Chicago, all of Ill.

[73] Assignee: Abbott Laboratories, Abbott Park, Ill.

[21] Appl. No.: 433,403

[22] Filed: Nov. 6, 1989

Related U.S. Application Data

[63] Continuation of Ser. No. 55,107, May 28, 1987, abandoned.

[51] Int. Cl.⁵ .......................... C12Q 1/32; C12N 9/99
[52] U.S. Cl. ........................ 435/26; 435/184; 436/174; 436/175; 436/176; 436/825; 252/95; 252/100; 252/186.1
[58] Field of Search ............. 435/4, 26, 184; 436/174, 175, 176, 825; 252/95, 100, 186.1

[56] References Cited

U.S. PATENT DOCUMENTS 4,145,406  3/1979  Schick et al. .................. 436/541 X
4,250,255  2/1981  Sanford ........................ 435/15
4,258,131  3/1981  Takagahara et al. ............ 435/26

FOREIGN PATENT DOCUMENTS 0352547  1/1990  European Pat. Off. .............. 435/26

OTHER PUBLICATIONS

Somero et al., Arch. Biochem Biophys., vol. 181, (1977) pp. 438-446.
Tietz, N. (ed), Textbook of Clinical Chemistry, 1986, pp. 148-149.
Forman et al, Journal of Biological Chemistry, vol. 252, No. 10 (1977) pp. 3379-3381.
Wilkinson, The Principles and Practice of Diagnostic Enzymology, (1976), pp. 46-54.
Isomune-LD®, Roche Diagnostic Systems, Nutley, N. J., Package Insert Apr., 1986.

Primary Examiner—Robert J. Warden
Assistant Examiner—Carol A. Spiegel
Attorney, Agent, or Firm—Daniel W. Collins

[57] ABSTRACT

A rapid and specific method and reagent for determining LD-1 isoenzyme in biological fluids by incorporating a chaotropic agent, such as sodium perchlorate, into an LDH assay reagent system. The chaotropic agent produces an immediate inactivation of the LDH isoenzymes containing one or more 'M' type subunits while the LTD-1 isoenzyme remains stable and is simultaneously measured.

14 Claims, 2 Drawing Sheets

METHOD AND REAGENT FOR DETERMINING LD-1 ISOENZYME

This application is a continuation of U.S. application Ser. No. 07/055,107, filed May 28, 1987, now abandoned.

BACKGROUND OF THE INVENTION

Lactic dehydrogenase (LDH) appears in human plasma and serum as five isoenzymes. These enzymes are tetrameric proteins composed of two subunit types 'M' (prevalent in skeletal Muscle) and 'H' (prevalent in the Heart). The isoenzymes were originally identified by electrophoretic separation and are conventionally referred to as LD-1, LD-2, LD-3, LD-4 and LD-5 based on their relative migration towards the anode, LD 1 being the fastest. Their corresponding subunit compositions are $H_4$, $H_3M$, $H_2M_2$, $HM_3$ and $M_4$ respectively.

The proportional amount of each isoenzyme varies considerably between organs, but within any given organ is relatively constant, such that each organ has a characteristic isoenzyme profile. For example, heart and erythrocytes have high proportions of LD-1 and LD-2, liver and skeletal muscle contain predominantly LD-5, and lung, kidney and brain contain mixtures in which LD-2, LD-3 and LD-4 may predominate to varying degrees. Leakage of these enzymes from a diseased or damaged organ will result in an elevation of total serum LDH, and further characterization of the serum isoenzyme composition can aid in identifying the organ responsible for this leakage. Thus, determinations of serum LDH and its isoenzyme composition are useful in the diagnosis of a variety of disease states. Diagnosis of suspected myocardial infarction is the most frequent application of LDH isoenzyme determinations. In these cases, an increase in the LD-1 isoenzyme relative to the other forms is specific and confirmatory for myocardial damage since the heart contains the largest proportion of the LD-1 enzyme.

Electrophoresis was the first method used to separate the LDH isoenzymes, and is still widely used to obtain complete isoenzyme profiles. This method has several disadvantages in that it requires multiple and lengthy steps, and expensive equipment. Separations using ion exchange columns have also been developed, but also have disadvantages.

An alternative approach to the analysis of LDH isoenzymes has been to selectively inhibit or denature some of the isoenzymes and so quantitate the relative proportion of those resistant to the treatment. Examples include: the use of urea, heat and high pH to progressively inactivate those isoenzymes containing the most 'M' subunits; the use of high substrate levels (pyruvate or lactate) to selectively inhibit the 'H' subunit; and the use of α-ketobutyric acid as a substrate specific for the H subunit.

U.S. Pat. No. 4,250,255 describes an approach where the total LDH activity is first measured and then the isoenzymes are selectively inhibited by treating the sample with an ionic amphiphile. The treated sample is then measured for enzyme activity and subtracted from the first measurement. The difference is the activity of the isoenzyme.

The subject invention provides an alternative to the above approaches and is a highly specific method for the determination of LD-1 isoenzyme in biological fluids.

SUMMARY OF THE INVENTION

The present invention is a rapid and specific method for quantitating LD-1 isoenzyme in biological fluid by incorporating a chaotropic agent into an LDH assay system. A method for determining the LD-1 isoenzyme activity of biological fluids comprises the single step of preparing a reaction mixture of the biological fluid and LDH reagent in the presence of a chaotrophic agent. The activity of LD-1 present in the reaction mixture can then be determined. The chaotropic agent is present in an amount sufficient to form from about 0.1 to about 5 molar solution in the reaction mixture, more preferably, from about 0.6 to about 1 molar solution. A particularly preferred chaotropic agent is sodium perchlorate. The LDH reagent can comprise a buffer, lactate and a chromogen or a buffer, pyruvate and a chromogen.

In another aspect, the present invention is directed toward a LD-1 assay reagent which comprises a buffer, a substrate, a chromogen and a chaotropic agent. The substrate can comprise lactate, pyruvate, NAD, NADH, or analogs thereof. The chromogen can also be NAD. Preferably, the chaotropic agent is sodium perchlorate which is present in an amount sufficient to form from about 0.1 to about 5 molar solution, preferably from about 0.6 to about 1 molar solution.

This new method and reagent system selectively assays LD-1 in biological fluid and provides improvements in speed, handling and accuracy at all levels of LD-1.

DETAILED DESCRIPTION OF THE INVENTION

Figure 1:
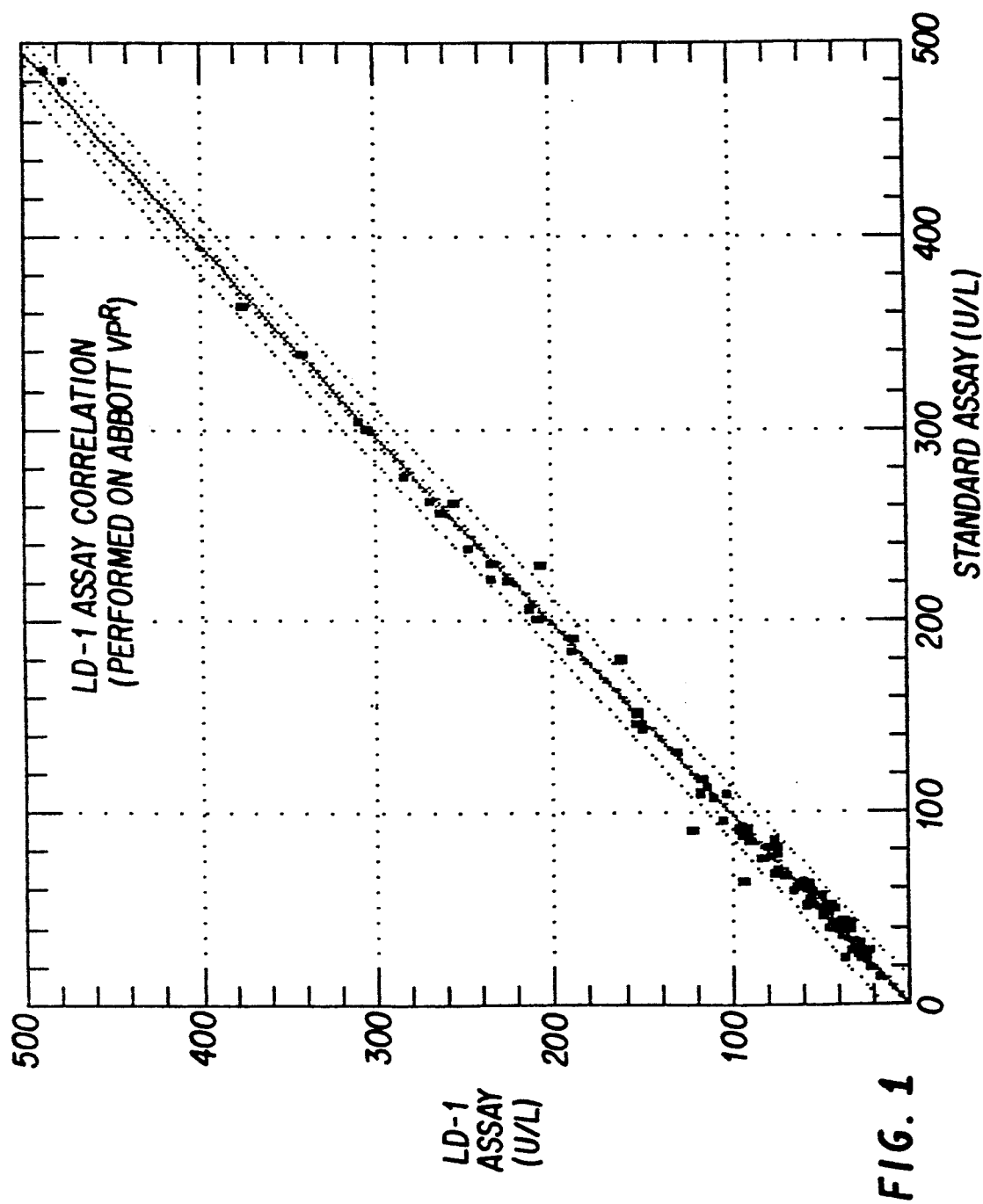
FIG. 1 shows the correlation of LD-1 assay results performed by the LD-1 assay of the subject method versus a multi step standard method on the Abbott VP ® clinical apparatus.

The subject invention is a reagent which selectively assays LD-1 in biological fluids. Biological fluids can include blood, plasma, serum, spinal fluid and urine. The reagent employs a chaotropic agent, such as sodium perchlorate, to selectively denature the LDH isoenzymes containing one or more 'M' type subunits and so remove their enzymatic activity. The reagent also contains the chemicals necessary for the simultaneous determination of the remaining LDH activity i.e., that due to LD-1. The quantitation of LD-1 as well as total LDH has been shown to be of value in diagnosing myocardial infarction, and in differentiating this disease from those involving LDH leakage from other organs.

The fundamental principal of this reagent is the ability of chaotropic agents to selectively disrupt the normal structural relationships of certain proteins as they exist in aqueous solution. Chaotropic agents are generally inorganic ions that have a large radius, a negative charge, and a low charge density; they are used to alter the secondary and tertiary structure of proteins. They are also known as the Hofmeister or lyotrophic series. They include anions with large partial molar ionic volumes (designated by the symbol Φ, and expressed in units of mL/mole), particularly those with volumes greater than 30 mL/mole. Examples are $TcO_4^-$, $ClO_4^-$, $ReO_4^-$, $BF_4^-$, $SeCN^-$, $SO_3F^-$, $SCN^-$, and $I^-$ (Wolff, J. and Maurey, J. R., *Biochim. Biophys. Acta* 69, 58–67 (1968)).

Generally, the chaotropic agent is employed in the biological sample in an amount sufficient to form from about a 0.1 to about a 5 molar solution in the total reaction mixture consisting of the biological sample and reagent. Preferably the chaotropic agent is present in an amount from about 0.6 to about 1.0 molar solution. The inclusion of the chaotropic agent in the biological fluid produces an immediate inactivation of all LDH isoenzymes containing one or more 'M' type subunits, LD-2 through LD-5. LD-1 remains stable and can be measured simultaneously with an LDH assay reagent.

The preferred chaotropic agent is sodium perchlorate ($NaClO_4$). Sodium perchlorate can reduce the affinity between the substrate (lactate or pyruvate) and the LD-1. The resulting decrease in reaction rate can be reversed by the addition of more substrate. For example, combining a 0.6 to about 1.0 molar solution of sodium perchlorate with 0.05 to about 0.5 molar solution of lactate yields a specific reagent for LD-1 providing a fast and accurate determination of LD-1.

In another aspect of the subject invention is a method for selectively removing non-LD-1 isoenzymes for reagent systems designed to assay LDH. Generally, the method involves adding a chaotropic agent to the reagent whereby the LD-2 through LD-5 isoenzymes are inactivated such that LD-1 can be quantified. Typically LDH assay reagents include a buffer, substrates (lactate, pyruvate NAD, NADH or analogs thereof) and optionally chromogens or indicator dyes. Basic LDH assay reagents are well known in the art and therefore, are not discussed in detail here. Commercially available LDH assay reagents which can be employed with the subject invention include A-GENT ® LDH-L, Abbott Laboratories, LIQUID STAT ® LD-L-VV by Beckman, FAST CHEM ® LDH-L by BMC, LDH-L-S V.R. Calibiochem, C-ZYME ® LDH by Coulter, COLORIMETRIX ® by Dow Chemical, LDH-L by Fisher, ULTRAZYME ® by Harleco, HMA LDH-VV by Hycel SPIN CHEM ® LDH-L by SKI, and LDH (L-P) by Worthington.

The LDH assay is based upon the general reaction as indicated below:

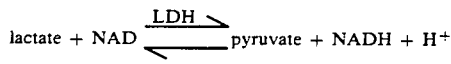

lactate + NAD $\underset{\longleftarrow}{\overset{LDH}{\longrightarrow}}$ pyruvate + NADH + H$^+$ The method consists of a reversible reaction where lactate is converted to pyruvate by the enzyme with concommitant reduction of NAD (nicotinamide-adenine dinucleotide) to NADH (reduced NAD). The rate of NADH formation or oxidation to NAD, in the case of the reverse reaction, as measured by the rate of absorbance increase at 340 nm, is thus directly proportional to LDH activity in the sample.

The subject method provides for both the selective inactivation of LD-2 through LD-5 and simultaneous assay of LD-1 activity. The entire procedure requires only as much time as is needed for a typical LDH total assay i.e., 4 minutes on the Abbott VP ® bichromatic analyzer and the Abbott SPECTRUM ® Diagnostic System (Abbott Laboratories, North Chicago, Ill.). Automated clinical analyzers employing bichromatic filters or detectors at 340/380 nm, such as the Abbott VP ® and Abbott Spectrum ® Instruments, are very appropriate for performing the assay with this reagent.

Typically 10 to 20 microliters (uL) of serum are added per 1 milliliter (ml) of reagent at 37° C., the Abbott instruments use 2.5–5.0 μL of serum and 0.25 ml of reagent, such that serum LDH and LD-1 activities ranging from 10 to 1000 units per liter (U/L) can be accurately determined.

The subject method requires no sample manipulation prior to the assay, apart from serum separation and aliquoting into sample cups on an instrument. The results are delivered in the same units as LDH total and refer to undiluted serum. No additional calculations are required. Also, because no sample manipulation is required such as dilution prior to assay the subject method maintains a very high degree of precision and accuracy.

In addition to inactivating isoenzymes LD-2 through LD-5, chaotropic agents reduce the affinity of LD-1 for lactate, pyruvate and their analogs. As a result, higher lactate concentrations are required in the presence of chaotropic agents than in its absence to obtain equal reaction rates with the same amount of LD-1 (all else being equal, and the reaction direction: lactate→pyruvate). By the same token, the inhibitions produced by pyruvate, oxalate and high levels of lactate are also diminished. Thus, the subject reagent specific for LD-1 which contains higher levels of substrate (i.e. lactate or pyruvate) will obtain greater linearity, due to a higher concentration of available substrate throughout the reaction time-frame, and a lower level of product inhibition arising during the same time-frame. An additional benefit of this phenomenon is the loss of interference in samples collected in anticoagulant tubes containing oxalate salts.

An additional advantage of the subject reagent and method is that it minimizes the sample volume required for an assay. Older immunologic and chromatographic methods require 200 and 1000 uL of serum sample respectively, all of which is consumed in the assay. The present method requires a maximum of 100 uL for manual assay, assuming that a 3.0 ml cuvette is required and typically only 2.5–5.0 ml of reagent is required for an automated assay. An automated assay may require that 50–100 uL of sample be in the sample cup, but the unused sample is available for other assays.

The subject invention is further illustrated by following examples which are not limitations thereof.

EXAMPLE 1

An LDH assay reagent was prepared specific for LD-1. First, a reagent powder was compounded, such that reconstitution with 30 milliliters of water per gram of powder yields the following concentrations of each active component:

| Ingredient | mmole/Liter of the Reconstituted Reagent |
| --- | --- |
| L-lactate | 47 |
| NAD | 7 |
| Tris(hydroxymethyl)aminoethane | 120 |
| Glutamic acid | 13 |

The L lactate and NAD are substrates and the Tris and glutamic acid buffer the resulting solution to pH 8.7. $Na_2EDTA$ may constitute 1% of the total powder weight to extend the stability of the NAD in solution. Sodium chloride may be used as an inert bulking agent to arrive at the required total weight of powder.

Second, a "diluent" solution was prepared containing 0.825 M sodium perchlorate and 0.165 M L-lactate in water; adjusted to pH 9.0 by the addition of sodium hydroxide.

Thirdly, a reagent specific for human LD-1 was prepared by dissolving 1.0 gram of the above powder per 30 mL of the "diluent", rather than water. This reconstituted reagent was used with the same assay configuration, samples and instruments as a total LDH assay reagent, but the resulting enzymatic activity measured was that due only to the LD-1 isoenzyme. Moreover, the activity units are directly proportional to those which would be measured if the same amount of pure LD-1 were to be assayed by the same powder but reconstituted with water.

EXAMPLE II

Other LD-1 assay reagents can be prepared from existing powder or liquid LDH assay reagents. The exact formulae for such diluent solutions can be arrived at by optimization studies, carried out as follows. A population of human serum samples, including those with elevated LDH and LD-1, are obtained and the LD-1 levels determined by established immunologic, electrophoretic or chromatographic methods for LD-1 determination (i.e the reference method). The data is correlated with those obtained by reconstituting an existing LDH reagent powder with various diluent solutions containing differing concentrations of L-lactate and/or sodium perchlorate (i.e. the experimental conditions).

The sodium perchlorate may range from 0.1 to about 5 molar solution, preferably from 0.5 to about 1.5 molar solution and the L-lactate from about zero to about 0.5 molar solution. The results of the LD-1 reference method are compared to each experimental condition using linear regression analysis, to obtain values for the slope, intercept and correlation coefficient for each comparison. An optimized LD-1 reagent can be derived from such analyses by the selection of the diluent formulation which yields a slope and correlation coefficient each approaching unity, and an intercept value approaching zero. The above procedure allows a preexisting powdered or lyophilized reagent formulation for total LDH to be easily adapted for the selective assay of the LD-1 isoenzyme. The results obtained from one human sample by both the total LDH and LD-1 assays can be readily combined to arrive at an LD-1:LDH ratio, which has been shown to be of diagnostic value. This method of assay of LD-1 may also be combined with assays for other human LDH isoenzymes or subunit compositions in such a way as to measure several other or all of the remaining LDH isoenzymes. Chaotropic agents may also be used to selectively assay isoenzymes of other clinically important enzymes.

EXAMPLE III

The following example demonstrates the excellent correlation between the subject reagent and method for the assay of LD-1 to a standard procedure for the isolation of serum LD-1 (ISOMUNE-LD ®, Roche Diagnostic Systems, Nutley, N.J.). One hundred and two serum samples were collected and aliquots from each sample were pretreated with the ISOMUNE-LD ® procedure and duplicate 5 and 10 microliter samples were assayed on the Abbott VP ® and Abbott SPECTRUM ® clinical analyzers, respectively, using Abbott A-Gent ®, LDH reagent. Duplicate aliquots of the untreated samples were also assayed with the subject LD-1 reagent as prepared in Example I on the same clinical analyzers; 2.5 and 5.0 microliters were used, respectively.

The Isomune-LD ® procedure isolates LD-1 and was performed as follows. To the aliquots of sample were added Anti LD-5 ($M_4$) Serum (goat), mixed and incubated for 5 minutes at ambient. Next a Second Antibody Suspension (donkey) was added to the aliquots, mixed and incubated for an additional 5 minutes at ambient and then centrifuged. The supernatants were then assayed to determine LD-1 isoenzyme activity with conventional reagents, in this case Abbott's A-GENT ® LDH L.

The subject method was employed to determine LD-1 concentration by merely combining the reagent prepared in Example 1 to each untreated aliquot and running on the clinical analyzer. Approximately 250 uL of reagent was employed to assay 2.5 uL of sample on the Abbott VP ® and 5.0 uL of sample on the Abbott SPECTRUM ®.

Figure 2:
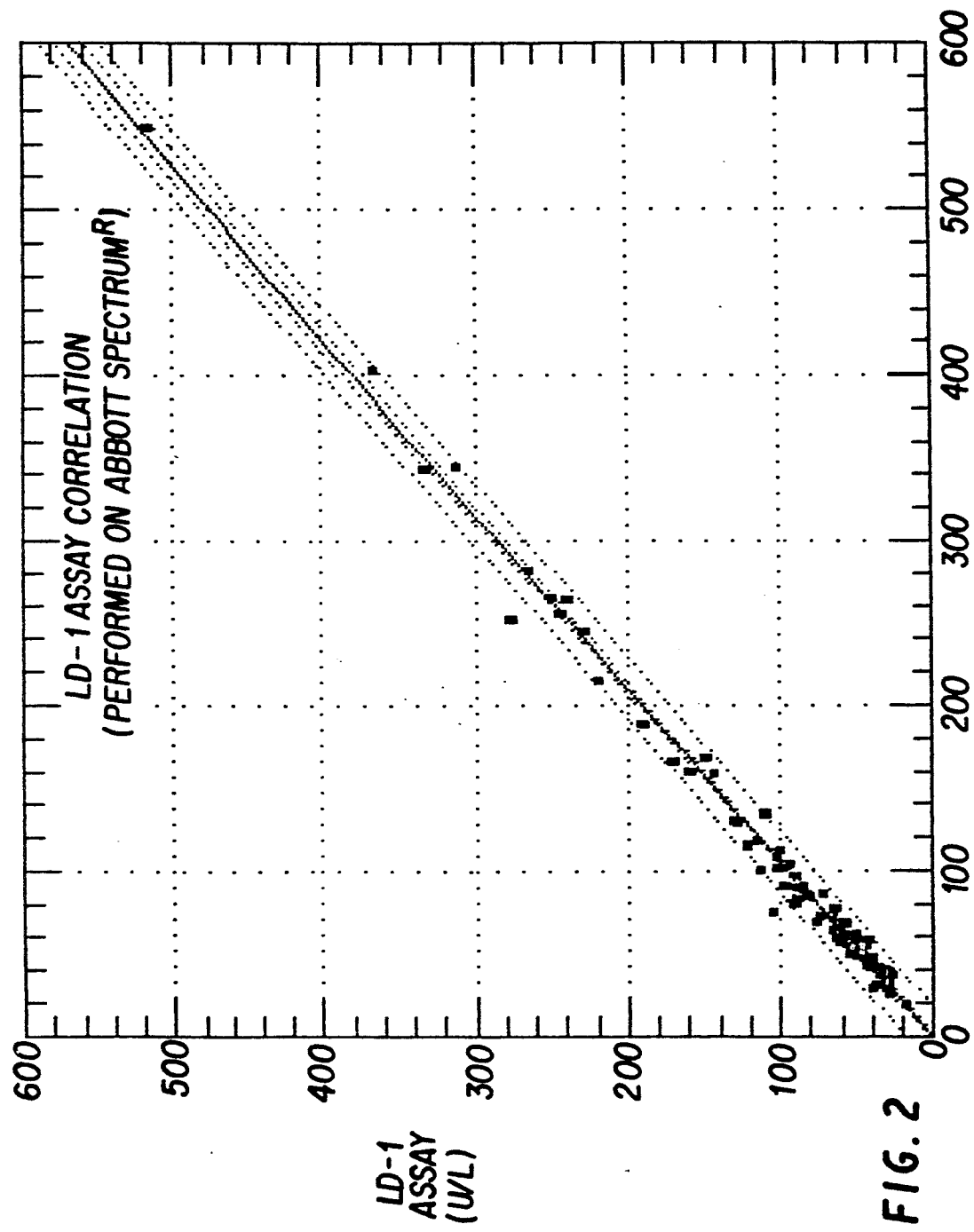
FIG. 2 shows the correlation of LD-1 assay results performed by the LD-1 assay of the subject method versus a multi-step standard method on the Abbott Spectrum ® clinical apparatus.

A computerized program determined the correlation of the two procedures on each clinical apparatus and graphed the results. The graphs appear as FIG. 1 for the assay conducted on the Abbott VP ® and FIG. 2 for the assays conducted on the Abbott SPECTRUM ®. The subject LD-1 assay results were graphed on the Y axis while the multi step standard assay results were graphed on the X axis. A perfect correlation would bisect the graph with a O intercept and a 1.0 slope. The correlation results were as follows:

|  | ABBOTT VP ® Standard* versus LD-1 Reagent** | ABBOTT SPECTRUM ® Standard* versus LD-1 Reagent** |
| --- | --- | --- |
| Intercept | −0.041 | 0.445 |
| Slope | 1.01 | 0.947 |
| Correlation | 0.997 | 0.994 |
| Number of samples | 102 | 92 |

*not subject matter of the present invention. LD-1 assay as performed with ISOMUNE-LD ® reagent to isolate LD-1 and then determined with A-GENT ® LDH reagent
**subject matter of the present invention The results indicate an excellent correlation between the multi step procedure which involved first isolating LD-1 from the serum sample and then measuring LD-1 activity versus the subject reagent and method which simultaneously isolates and measures the LD-1 activity.

We claim:

1. A method for determining LD-1 isoenzyme activity in a biological fluid, said method comprising the steps of:
   (a) preparing a reaction mixture of a biological fluid and an LDH reagent in the presence of an inorganic anionic chaotropic agent, said inorganic anionic chaotropic agent having a partial molal ionic volume of about 30 mL/mole or greater, wherein the inorganic anionic chaotropic agent substantially inhibits the activities of LDH isoenzymes containing one or more M subunits 4, and wherein said LD-1 isoenzyme is free from any M subunit; and
   (b) determining the activity of LD-1 isoenzyme present in the reaction mixture.

2. The method of claim 1 wherein said inorganic anionic chaotropic agent is present in an amount of from about 0.1 to about 5 molar solution in the reaction mixture.

3. The method of claim 2 wherein said anionic chaotropic agent is present in an amount sufficient to form from about 0.6 to about 1 molar solution in the reaction mixture.

4. The method of claim 2 wherein said inorganic chaotropic agent is sodium perchlorate.

5. The method of claim 1 wherein said reagent comprises a buffer, lactate, and a chromogen, wherein said chromogen provides a detectable spectrophotometric change in response to the reaction of LD-1 with lactate.

6. The method of claim 1 wherein said reagent comprises a buffer, pyruvate, and a chromogen, wherein said chromogen provides a detectable spectrophotometric change in response to the reaction of LD-1 with pyruvate.

7. The method of claim 1 wherein said inorganic anionic chaotropic agent is selected from the group consisting of $TcO_4^-$, $ClO_4^-$, $ReO_4^-$, $BF_4^-$, $SO_3F^-$, $SeCN^-$, $SCN^-$ and $I^-$.

8. An LD-1 isoenzyme assay reagent comprising: a buffer, a substrate for LDH, a chromogen, and an inorganic anionic chaotropic agent, said inorganic anionic chaotropic agent having a partial molal ionic volume of about 30 mL/mole or greater, wherein said chromogen provides a detectable spectrophotometric change in response to the reaction of LD-1 with said substrate.

9. The LD-1 assay reagent of claim 8 wherein said substrate for LDH is lactate or pyruvate, and said chromogen is NAD or NADH, wherein said chromogen provides a detectable spectrophotometric change in response to the reaction of LD-1 with said substrate.

10. The LD-1 assay reagent of claim 8 wherein said chromogen is NAD which provides a detectable spectrophotometric change in response to the reaction of LD-1 with said substrate.

11. The LD-1 isoenzyme assay reagent of claim 8 wherein said anionic chaotropic agent is sodium perchlorate.

12. The LD-1 isoenzyme assay reagent of claim 8 wherein said anionic chaotropic agent is present in an amount sufficient to form from about 0.1 to about 5 molar solution.

13. The LD-1 isoenzyme assay reagent of claim 12 wherein said anionic chaotropic agent is present in an amount sufficient to form from about 0.6 to about 1 molar solution.

14. The LD-1 assay reagent of claim 8 wherein said inorganic anionic chaotropic agent is selected from the group consisting of $TcO_4$, $ClO_4$, $ReO_4$, $BF_4$, $SO_3F$, $SeCN^-$, $SCN^-$ and $I^-$.

* * * * *